(12) United States Patent
Chen et al.

(10) Patent No.: US 11,630,097 B2
(45) Date of Patent: Apr. 18, 2023

(54) QUANTITATIVE EVALUATION METHOD FOR WORKABILITY OF CONCRETE BASED ON BOTTOM RESISTANCE ANALYSIS

(71) Applicant: GUANGXI UNIVERSITY, Guangxi (CN)

(72) Inventors: Zheng Chen, Guangxi (CN); Ben Chen, Guangxi (CN); Changjie Wu, Guangxi (CN); Zhongxing Zou, Guangxi (CN); Xin Sun, Guangxi (CN)

(73) Assignee: GUANGXI UNIVERSITY, Guangxi (CN)

( * ) Notice: Subject to any disclaimer, the term of this patent is extended or adjusted under 35 U.S.C. 154(b) by 0 days.

(21) Appl. No.: 17/442,630

(22) PCT Filed: Dec. 28, 2020

(86) PCT No.: PCT/CN2020/140306
§ 371 (c)(1),
(2) Date: Sep. 24, 2021

(87) PCT Pub. No.: WO2021/248881
PCT Pub. Date: Dec. 16, 2021

(65) Prior Publication Data
US 2022/0326213 A1    Oct. 13, 2022

(30) Foreign Application Priority Data

Jun. 9, 2020  (CN) .......................... 202010518294.2
Sep. 7, 2020  (CN) .......................... 202010930732.6

(51) Int. Cl.
*G01N 33/38*  (2006.01)
*G01N 1/28*   (2006.01)
*G01N 1/38*   (2006.01)

(52) U.S. Cl.
CPC ........... *G01N 33/383* (2013.01); *G01N 1/286* (2013.01); *G01N 1/38* (2013.01); *G01N 2001/386* (2013.01)

(58) Field of Classification Search
CPC .......... B01F 15/00162; B01F 15/00188; B01F 15/00201; B01F 15/00246; G01N 33/383;
(Continued)

(56) References Cited

U.S. PATENT DOCUMENTS 1,651,596 A * 12/1927 Hall ........................ G01N 11/10
                                                      73/54.36
2,247,553 A *  7/1941 Hutchinson ............ G01N 11/02
                                                      73/594
(Continued)

FOREIGN PATENT DOCUMENTS

CN    101251529    8/2008
CN    201945535    8/2011
(Continued)

OTHER PUBLICATIONS

"International Search Report (Form PCT/ISA/210)" of PCT/CN2020/140306, dated Mar. 30, 2021, pp. 1-5.
(Continued)

*Primary Examiner* — David A. Rogers
(74) *Attorney, Agent, or Firm* — JCIP Global Inc.

(57) ABSTRACT

The present invention relates to a quantitative evaluation method for concrete workability based on bottom resistance, including the following steps: step 1, carrying out a test for bottom resistance of fresh concrete; step 2, drawing a curve of inserting velocity of steel sheet over time; and step 3, quantitatively evaluating a concrete workability based on conditions of the bottom resistance. This method can quantitatively characterize the sinking condition of aggregate of the fresh concrete by effectively carrying out the test for
(Continued)

bottom resistance of fresh concrete, calculating the inserting velocity of concrete and drawing the curves of displacement and velocity over time, so as to achieve the quantitative evaluation for concrete workability and overcome the defects of conventional methods that it is difficult to quantitatively characterize the segregation degree of concrete.

4 Claims, 3 Drawing Sheets

(58) Field of Classification Search
CPC .......... G01N 2011/0046; G01N 11/10; G01N 11/00; G01N 9/36; G01N 2011/006; G01N 33/38
See application file for complete search history.

(56) References Cited

U.S. PATENT DOCUMENTS

| | | | | |
|---|---|---|---|---|
| 2,630,706 | A * | 3/1953 | Maxon, Jr. | G01N 11/10 73/54.03 |
| 3,069,900 | A * | 12/1962 | Kimberly | E21B 21/08 73/54.32 |
| 3,631,712 | A * | 1/1972 | Mercier | G01N 33/383 73/54.03 |
| 3,688,588 | A * | 9/1972 | Hill | G01N 9/10 73/451 |
| 3,863,494 | A * | 2/1975 | Nasser | G01N 33/383 73/54.03 |
| 3,924,447 | A * | 12/1975 | Garrison | B28C 5/422 73/54.03 |
| 4,112,742 | A * | 9/1978 | Zahn | G01N 33/26 73/54.01 |
| 4,193,291 | A * | 3/1980 | Lynnworth | G01N 9/00 376/245 |
| 4,356,723 | A * | 11/1982 | Fay | G01N 11/00 73/54.03 |
| 4,578,989 | A * | 4/1986 | Scott | G01N 33/383 33/379 |
| 4,843,868 | A * | 7/1989 | Propst | G01N 33/383 73/61.72 |
| 4,900,154 | A * | 2/1990 | Waitzinger | G01N 33/383 366/40 |
| 4,915,297 | A * | 4/1990 | Norman | B28C 7/003 122/20 A |
| 4,981,042 | A * | 1/1991 | Reeves | G01N 9/16 73/454 |
| 5,086,646 | A * | 2/1992 | Jamison | G01N 9/00 73/61.63 |
| 5,437,181 | A * | 8/1995 | Nasser | G01N 33/383 73/54.01 |
| 5,541,855 | A * | 7/1996 | Enzler | G01N 11/14 73/803 |
| 5,695,280 | A * | 12/1997 | Baker | B28C 7/0007 366/27 |
| 5,948,970 | A * | 9/1999 | Te'eni | B28B 23/0031 73/54.23 |
| 6,227,039 | B1 * | 5/2001 | Te'eni | B28C 7/024 73/53.04 |
| 6,918,292 | B2 * | 7/2005 | Go Boncan | G01N 33/383 73/866 |
| 6,957,586 | B2 * | 10/2005 | Sprague | G01F 1/3259 73/32 R |
| 7,240,545 | B1 * | 7/2007 | Jennings | G01F 22/00 73/866 |
| 7,384,180 | B2 * | 6/2008 | Jarvinen | G01N 33/383 366/601 |
| 7,484,912 | B1 * | 2/2009 | Cheek | B28B 7/0094 404/133.1 |
| D638,729 | S * | 5/2011 | Beaupre | D10/78 |
| 8,020,431 | B2 * | 9/2011 | Cooley | B28C 5/4231 366/60 |
| 8,118,473 | B2 * | 2/2012 | Compton | B28C 7/12 700/265 |
| 8,818,561 | B2 * | 8/2014 | Koehler | G01N 33/383 700/265 |
| 9,199,391 | B2 * | 12/2015 | Beaupre | B28C 7/024 |
| 9,511,510 | B2 * | 12/2016 | Roy | B28C 7/02 |
| 9,550,312 | B2 * | 1/2017 | Roberts | B28C 7/0454 |
| 9,702,863 | B2 * | 7/2017 | Beaupré | G01N 33/383 |
| 10,052,794 | B2 * | 8/2018 | Beaupré | B28C 7/12 |
| 10,126,288 | B2 * | 11/2018 | Radjy | G01N 33/383 |
| 10,183,418 | B2 * | 1/2019 | Jordan | B28C 5/422 |
| 10,363,684 | B2 * | 7/2019 | Roberts | B28C 5/422 |
| 10,429,285 | B2 * | 10/2019 | Uusivirta | G01N 11/00 |
| 10,520,410 | B2 * | 12/2019 | Beaupre | G01N 11/10 |
| 10,527,534 | B2 * | 1/2020 | McAnally | G01N 29/348 |
| 11,041,794 | B2 * | 6/2021 | Beaupre | G01N 11/10 |
| 11,385,153 | B2 * | 7/2022 | Roberts | B28C 7/0404 |
| 11,402,312 | B2 * | 8/2022 | Beaupre | B28C 7/024 |
| 11,420,358 | B2 * | 8/2022 | Beaupre | G01N 11/14 |
| 2005/0087002 | A1 * | 4/2005 | Kanzaki | B01F 33/453 73/54.28 |
| 2007/0023551 | A1 * | 2/2007 | Aichinger | C04B 2/066 241/34 |
| 2007/0295104 | A1 * | 12/2007 | Ellegood | G01F 1/28 73/861.79 |
| 2009/0037026 | A1 * | 2/2009 | Sostaric | B28B 23/0031 700/265 |
| 2011/0004332 | A1 * | 1/2011 | Andersen | C04B 40/0032 700/265 |
| 2011/0077778 | A1 * | 3/2011 | Berman | G05B 15/02 700/265 |
| 2012/0186341 | A1 * | 7/2012 | Oike | G01D 5/165 73/317 |
| 2015/0078417 | A1 * | 3/2015 | Verdino | G01K 1/024 374/142 |
| 2015/0355160 | A1 * | 12/2015 | Berman | G01N 27/048 73/54.03 |
| 2016/0025700 | A1 * | 1/2016 | Beaupré | B28C 5/422 73/32 R |
| 2017/0108421 | A1 * | 4/2017 | Beaupre | G01N 11/14 |
| 2017/0217047 | A1 * | 8/2017 | Leon | B28C 5/4231 |
| 2018/0100791 | A9 * | 4/2018 | Beaupre | G01N 11/14 |
| 2018/0319040 | A1 * | 11/2018 | Beaupre | B01F 23/511 |
| 2020/0078987 | A1 * | 3/2020 | Beaupre | G01N 33/383 |
| 2020/0225258 | A1 * | 7/2020 | Beaupre | G01P 3/48 |
| 2020/0232966 | A1 * | 7/2020 | Beaupre | G01N 33/383 |
| 2020/0282597 | A1 * | 9/2020 | Beaupre | C04B 40/0028 |
| 2021/0001765 | A1 * | 1/2021 | Beaupre | B28C 5/422 |
| 2021/0031407 | A1 * | 2/2021 | Roberts | B28C 7/026 |
| 2021/0031408 | A1 * | 2/2021 | Beaupre | B28C 7/024 |
| 2021/0055195 | A1 * | 2/2021 | Beaupre | B28C 7/024 |
| 2021/0178632 | A1 * | 6/2021 | Bollin | B28C 7/12 |
| 2021/0187786 | A1 * | 6/2021 | Beaupre | B28C 5/4217 |
| 2022/0120651 | A1 * | 4/2022 | Fahmi | G01N 11/10 |

FOREIGN PATENT DOCUMENTS

| | | | | |
|---|---|---|---|---|
| CN | 109115679 A | * | 1/2019 | ........... G01M 10/00 |
| CN | 208621466 | | 3/2019 | |
| CN | 110736826 | | 1/2020 | |
| CN | 111811934 | | 10/2020 | |
| CN | 111912746 | | 11/2020 | |
| JP | 2000162109 | | 6/2000 | |

OTHER PUBLICATIONS

"Written Opinion of the International Searching Authority (Form PCT/ISA/237)" of PCT/CN2020/140306, dated Mar. 30, 2021, pp. 1-4.

* cited by examiner

QUANTITATIVE EVALUATION METHOD FOR WORKABILITY OF CONCRETE BASED ON BOTTOM RESISTANCE ANALYSIS

CROSS-REFERENCE TO RELATED APPLICATION

This application is a 371 of international application of PCT application serial no. PCT/CN2020/140306, filed on Dec. 28, 2020, which claims the priority benefit of China application no. 202010930732.6, filed on Sep. 7, 2020 and China application no. 202010518294.2, filed on Jun. 9, 2020. The entirety of each of the above mentioned patent applications is hereby incorporated by reference herein and made a part of this specification.

TECHNICAL FIELD

The present invention relates to a quantitative evaluation method for concrete workability, and specifically relates to a quantitative evaluation method for concrete workability based on bottom resistance analysis.

BACKGROUND

In civil engineering construction, in order to obtain dense and uniform concrete structure and facilitate construction operation (mixing, transportation, pouring, vibration and other processes), fresh concrete must have good construction performance, which is called workability of concrete. The connotation of workability of concrete mixture is complex, including several aspects such as fluidity, cohesion and water retention. The fresh concrete with poor workability has the phenomena of delamination, segregation and bleeding, which has a great negative impact on the construction process and process quality.

Therefore, in order to ensure the project quality and smooth construction, it is necessary to evaluate the workability of fresh concrete in all aspects.

At present, the workability of concrete mixture is difficult to be fully and properly expressed by a simple measurement method and index. Particularly, the fluidity can be measured quantitatively by experiment, and its determination methods include slump method and Vebe consistency method. However, this method has no specific quantitative characterization of its cohesion and water retention, and lacks the comprehensiveness for evaluating the concrete workability.

For the evaluation of cohesion, working performance of the fresh concrete can be indirectly characterized by using a rotary rheometer to measure the plastic viscosity and yield stress. However, the conditions for indirectly evaluating the cohesion through the rheological properties of concrete are relatively stringent. The expensive price and huge equipment volume of this method limit its scope of application to the laboratory, which is lack of economic efficiency and convenience.

At the same time, the actual construction site basically evaluates the cohesion and water retention of fresh concrete by visual inspection and construction experience. The test results often fluctuate greatly with the differences of testers. This method is lack of accuracy and cannot be quantitatively standardized.

Fresh concrete with poor workability is prone to bleeding and segregation. Generally, these two phenomena occur at the same time. As soon as the concrete is bleeding, the water and mud float upward, and the sinking stones are tightly bonded with the base, which will greatly increase the resistance to insert into the bottom of the concrete.

SUMMARY

In order to evaluate the cohesion and water retention of fresh concrete, the present invention provides a quantitative evaluation method for concrete workability based on bottom resistance analysis. By quantifying the sinking conditions of aggregate of the fresh concrete, the cohesion and water retention of fresh concrete can be quantitatively evaluated, and thereby evaluating the comprehensive working performance of concrete by combining the slump. By this method, inserting displacement to bottom and velocity for concrete in different status are measured through a test for bottom resistance, characterization for workability of concrete is obtained and analyzed, so as to quantitatively evaluate the workability of fresh concrete conveniently and rapidly.

The above-mentioned objectives are achieved by the following technical solutions of the present invention: a quantitative evaluation method for concrete workability based on bottom resistance analysis, including the following steps:

step 1: carrying out a test for a bottom resistance of fresh concrete: placing a concrete container on a level platform, filling with the fresh concrete which has been already mixed evenly, removing a residual concrete from a surface of the container and vibrating sufficiently, inserting a steel sheet into a bottom of the concrete, recording a displacement of the steel sheet and a corresponding time;

step 2: drawing a curve of inserting velocity of the steel sheet over time: drawing a curve of displacement of the steel sheet over time based on the data of the displacement of the steel sheet and the corresponding time, and by deriving the curve of the displacement of the steel sheet over time to analyze the inserting velocity and time, then drawing the curve of the inserting velocity of the steel sheet over time; and step 3, quantitatively evaluating the concrete workability based on conditions of the bottom resistance: based on the curve of the displacement of the steel sheet over time determined by the test for the bottom resistance, evaluating the concrete workability by using a calculation model of coefficient of the colligation for concrete workability to solve the coefficient of the colligation for the concrete workability, the calculation model of the coefficient of the colligation for the concrete workability is as follows by integral calculation with an interval of v>100 mm/s:

$$W = \sum_{i=1}^{n} \int_{t_{i1}}^{t_{i2}} v(t)dt$$

wherein W is the coefficient of the colligation for the concrete workability, n is a number of the interval, $t_{i1}$ is a starting-point of the interval, $t_{i2}$ is an end-point of the interval, i=1, 2, ..., n.

Water and slurry float up from a segregated bleeding concrete, and sinking stones cement with a base tightly, resistance of aggregate is resulted at the bottom, and by determining a segregation degree of the concrete through a degree of the aggregate sank, cohesion and water retention of the concrete workability are quantitatively evaluated.

Further, the test for bottom resistance of fresh concrete is as follows:

mixing water, cement, grit, crushed stones and a water reducer according to a ratio to prepare the fresh concrete for use, wherein a mass ratio of the water, the cement, the grit to the crushed stones is 1:2.01:4.57:5.90, adding the water reducer having a gelling material mass of 0.22%-0.66%, filling the concrete container with the fresh concrete, upon sufficient vibration, wiping up the surface of the concrete container, fixing the steel sheet and a spring to a digital caliper with screws, pulling a vernier of the caliper to the bottom by using an insertion force provided by the spring, allowing the spring to be in a stress state, releasing the vernier so that a steel ruler on the vernier is inserted to the bottom of concrete with the coiled spring, and automatically recording the displacement of the steel sheet and the corresponding time by connecting the digital caliper to a computer.

Further, the test for bottom resistance of fresh concrete is as follows:

mixing water, cement, grit, crushed stones and a water reducer according to a ratio to prepare the fresh concrete for use, wherein a mass ratio of the water, the cement, the grit to the crushed stones is 1:2.01:4.57:5.90, and adding the water reducer having a gelling material mass of 0.44%; wherein the concrete at this moment has good flowability, and no segregation or bleeding occurs in the concrete through visual inspection; filling the concrete container with the fresh concrete, upon sufficient vibration, wiping up the surface of the concrete container, fixing the steel sheet and a spring to a digital caliper with screws, pulling a vernier of the caliper to the bottom by using an insertion force provided by the spring, allowing the spring to be in a stress state, releasing the vernier so that a steel ruler on the vernier is inserted to the bottom of concrete with the coiled spring, and automatically recording the displacement of the steel sheet and the corresponding time by connecting the digital caliper to a computer.

The outstanding advantages of the present invention lie in that:

A quantitative evaluation method for concrete workability which is not limited to the using site is provided, and such method can quantify the sinking conditions of aggregate of the fresh concrete, and quantitatively evaluate the cohesion and water retention of the concrete. This method is simple and fast, overcomes the defect that the conventional slump method cannot quantitatively evaluate the segregation and bleeding of concrete, and quantitatively characterizes the segregation and bleeding of concrete through the calculation model of coefficient of colligation for concrete workability. It has important academic significance and engineering application value for comprehensively evaluating and judging the workability of fresh concrete under the conditions of field test in engineering construction.

DETAILED DESCRIPTION

The technical solutions of the present invention are further described in detail in combination with the following embodiments and accompanied drawings.

Embodiment 1

Figure 1:
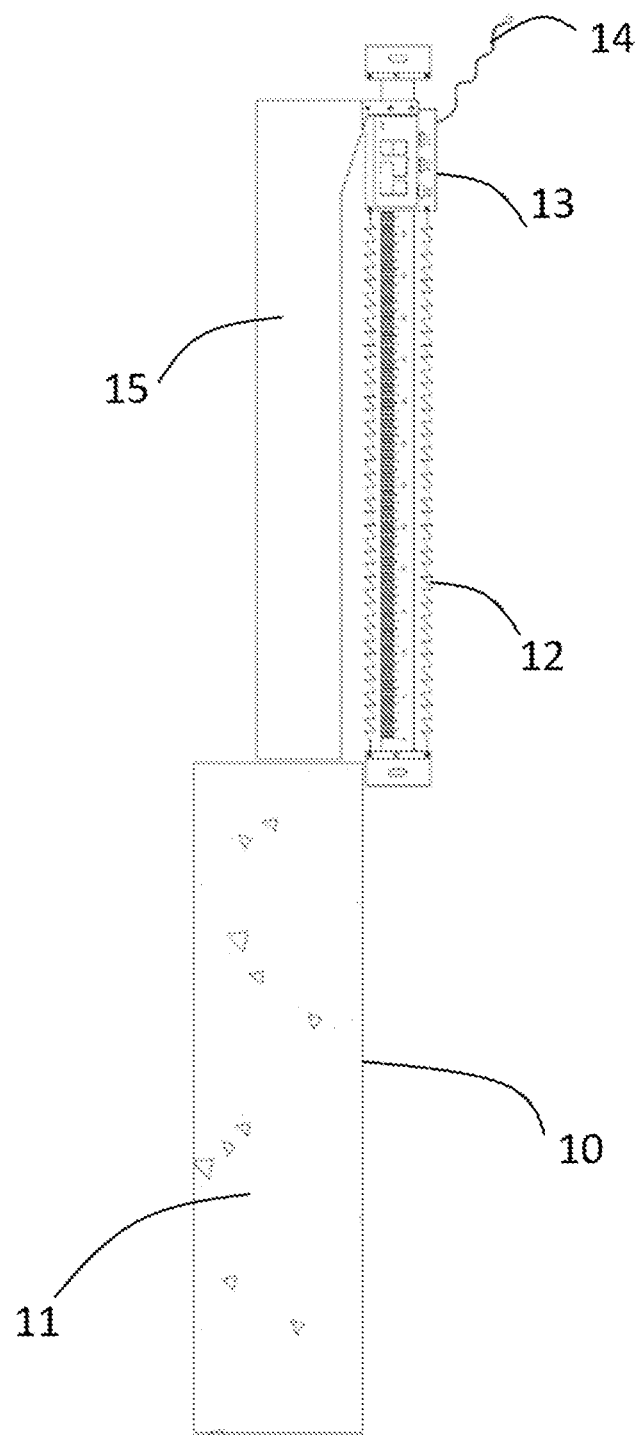
FIG. 1 is a schematic diagram of tests for bottom resistance in Embodiments 1 and 2.

A quantitative evaluation method for concrete workability based on bottom resistance according to the present invention included the following steps:

Step 1: carrying out a test for a bottom resistance of fresh concrete 11:

water, cement, grit, crushed stones and a water reducer were mixed according to a ratio to prepare a fresh concrete 11 for use, wherein a mass ratio of the water, the cement, the grit to the crushed stones was 1:2.22:3.65:4.65. The water reducer having a gelling material mass of 0.44% was added. The concrete at this moment had severe segregation and bleeding. A concrete container 10 was filled with the fresh concrete 11, and upon sufficient vibration, surface of the concrete container 10 was wiped up. A steel sheet 15 and a spring 12 were fixed to a digital caliper 13 with screws, and an insertion force was provided by the spring 12 shown as FIG. 1. A vernier of the caliper 13 was pulled to the bottom, allowing the spring 12 to be in a stress state, and the vernier was released so that a steel ruler on the vernier was inserted to the bottom of concrete with the coiled spring 12. Displacement of steel sheet 15 and a corresponding time were automatically recorded by connecting the digital caliper 13 to a computer.

Figure 2:
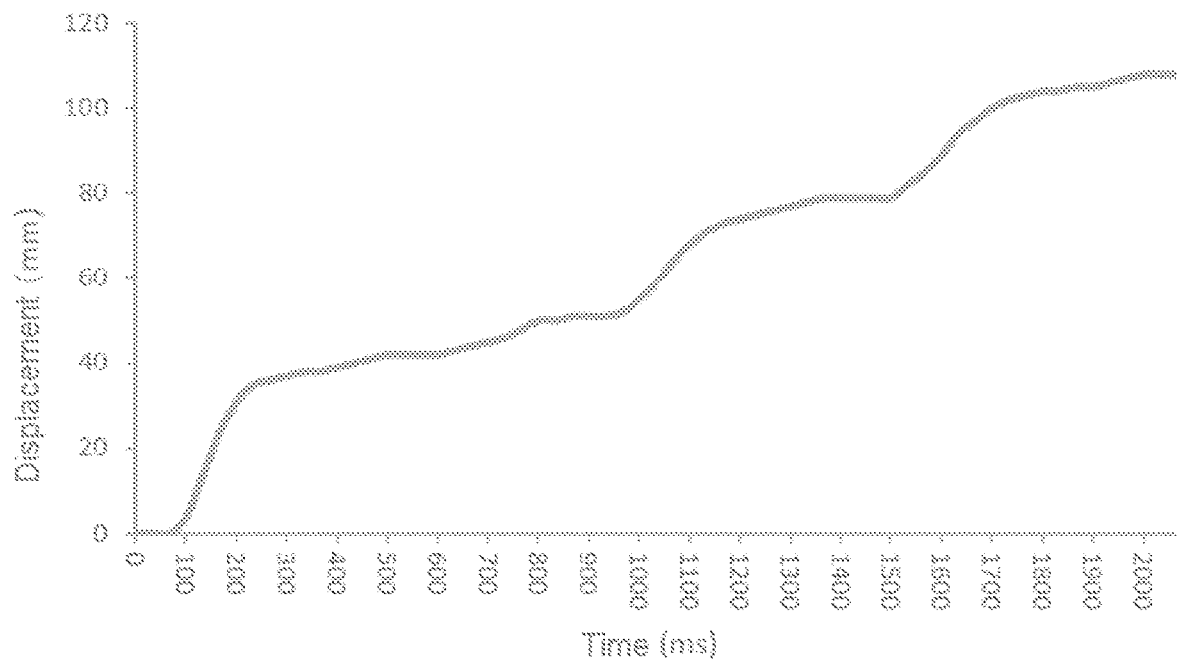
FIG. 2 is a schematic diagram of a curve of displacement of steel sheet over time in Embodiment 1.
Figure 3:
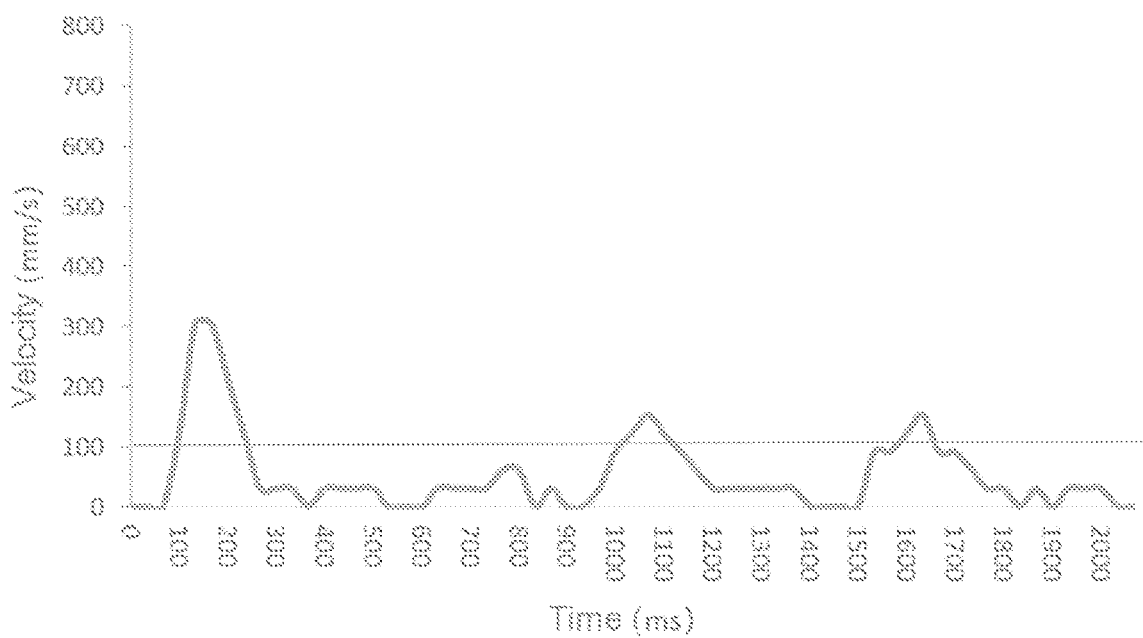
FIG. 3 is a schematic diagram of a curve of inserting velocity of steel sheet over time in Embodiment 1.

Step 2: drawing a curve of inserting velocity of steel sheet 15 over time:

a curve of displacement of steel sheet 15 over time was drawn based on the data of the displacement of steel sheet 15 and the corresponding time, and by deriving the curve of displacement of steel sheet 15 over time to analyze the inserting velocity and time, then a curve of inserting velocity of steel sheet 15 over time was drawn, shown as FIG. 2 and FIG. 3.

Step 3: quantitatively evaluating a concrete workability based on conditions of the bottom resistance:

based on the curve of displacement of steel sheet 15 over time determined by the test for bottom resistance, coefficient of colligation for concrete workability W was determined by using a calculation model of coefficient of colligation for concrete workability which was 45 mm, and a corresponding slump was 200 mm and a divergence was 640*520. Severe segregation and bleeding were observed in the concrete already.

Embodiment 2

A quantitative evaluation method for concrete workability based on bottom resistance according to the present invention included the following steps:

Step 1: carrying out a test for bottom resistance of fresh concrete 11:

water, cement, grit, crushed stones and a water reducer were mixed according to a ratio to prepare a fresh concrete 11 for use, wherein a mass ratio of the water, the cement, the grit to the crushed stones was 1:2.01:4.57:5.90. The water reducer having a gelling material mass of 0.44% was added. The concrete at this moment had good flowability, and no segregation or bleeding occurred in the concrete through visual inspection. A concrete container 10 was filled with the fresh concrete 11, and upon sufficient vibration, surface of the concrete container 10 was wiped up. A steel sheet 15 and a spring 12 were fixed to a digital caliper 13 with screws, and an insertion force was provided by the spring 12 shown as FIG. 1. A vernier of the caliper 13 was pulled to the bottom, allowing the spring 12 to be in a stress state, and the vernier was released so that a steel ruler on the vernier was inserted to the bottom of concrete with the coiled spring 12. Displacement of steel sheet 15 and a corresponding time were automatically recorded by connecting the digital caliper 13 to a computer.

Figure 4:
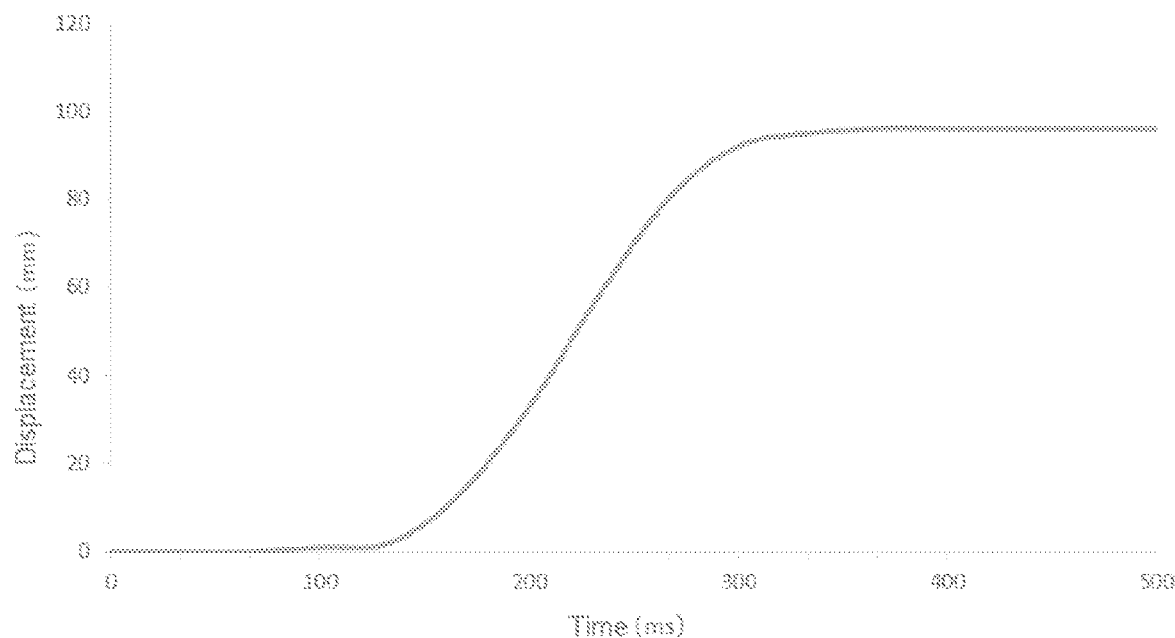
FIG. 4 is a schematic diagram of a curve of displacement of steel sheet over time in Embodiment 2.
Figure 5:
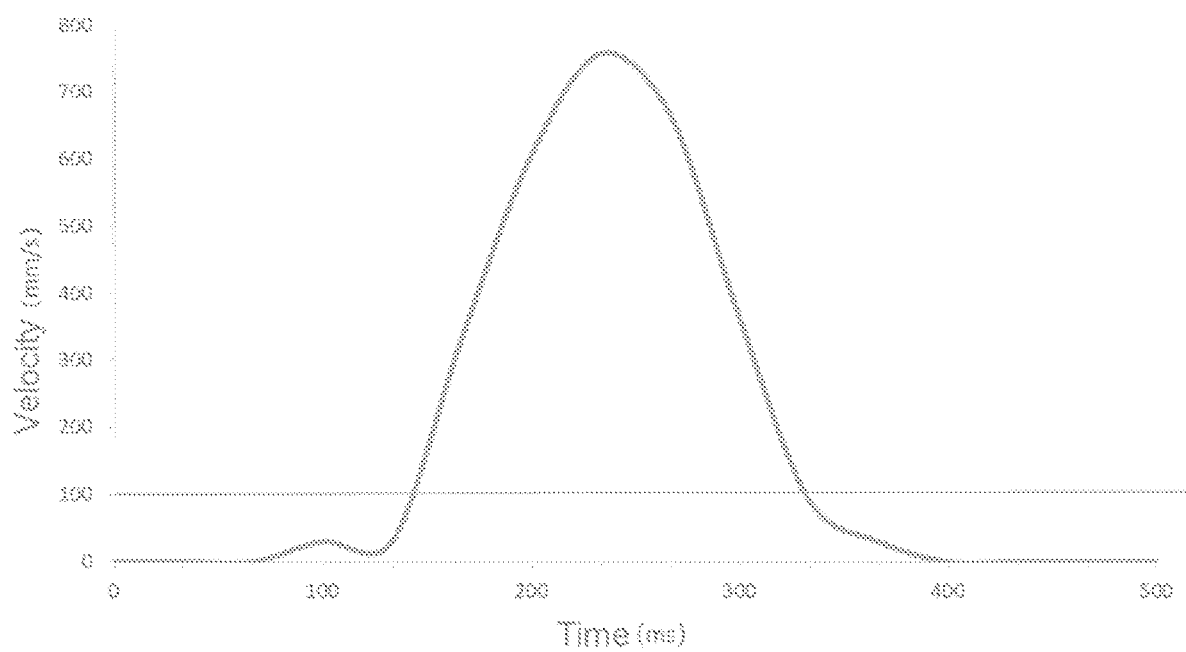
FIG. 5 is a schematic diagram of a curve of inserting velocity of steel sheet over time in Embodiment 2.

Step 2: drawing a curve of inserting velocity of steel sheet 15 over time:

a curve of displacement of steel sheet 15 over time was drawn based on the data of the displacement of steel sheet 15 and the corresponding time, and by deriving the curve of displacement of steel sheet 15 over time to analyze the inserting velocity and time, then a curve of inserting velocity of steel sheet 15 over time was drawn, shown as FIG. 4 and FIG. 5.

Step 3: quantitatively evaluating a concrete workability based on conditions of the bottom resistance:

based on the curve of displacement of steel sheet 15 over time determined by the test for bottom resistance, coefficient of colligation for concrete workability W was determined by using a calculation model of coefficient of colligation for concrete workability which was 71 mm, and a corresponding slump was 200 mm and a divergence was 450*470. Good workability was observed in the concrete.

Multiple groups of tests were carried out according to the same steps as above, and test results are shown in the table below:

TABLE 1

| Group | Water | Cement | Grit | Stones | Water reducer | Workability condition | Slump, Divergence (mm) | Test result |
|---|---|---|---|---|---|---|---|---|
| 1 | 1 | 2.01 | 4.57 | 5.90 | 0.22% | No segregation or bleeding | 140, 400 * 380 | 95 mm |
| 2 | 1 | 2.01 | 4.57 | 5.90 | 0.44% | No segregation or bleeding | 200, 470 * 450 | 71 mm |
| 3 | 1 | 2.01 | 4.57 | 5.90 | 0.66% | Slight segregation and bleeding | 200, 540 * 520 | 64 mm |
| 4 | 1 | 2.01 | 4.57 | 5.90 | 1% | Severe segregation and bleeding | 240, 700 * 650 | 53 mm |
| 5 | 1 | 2.22 | 3.65 | 4.65 | 0.44% | Severe segregation and bleeding | 200, 640 * 520 | 45 mm |

The test results show that under the condition of the same ratio, the concrete workability was changed by varying an addition amount of the water reducer. As the water reducer was increased, the condition of concrete changed from poor flowability to good workability, and then to severe segregation and bleeding. The test results decrease with the aggravation of concrete segregation and bleeding, and have good discrimination, which can better quantitatively evaluate the workability of concrete.

What is claimed is:

1. A quantitative evaluation method for concrete workability based on bottom resistance analysis, comprising the following steps:

step 1: carrying out a test for a bottom resistance of fresh concrete: placing a concrete container on a level platform, filling with the fresh concrete which has been already mixed evenly, removing a residual concrete from a surface of the container and vibrating, inserting a steel sheet into a bottom of the concrete, recording a displacement of the steel sheet and a corresponding time;

step 2: drawing a curve of inserting velocity of the steel sheet over time: drawing a curve of displacement of the steel sheet over time based on the data of the displacement of the steel sheet and the corresponding time, and by deriving the curve of the displacement of the steel sheet over time to analyze the inserting velocity and time, then drawing the curve of the inserting velocity of the steel sheet over time; and step 3: quantitatively evaluating the concrete workability based on conditions of the bottom resistance: based on the curve of the displacement of the steel sheet over time determined by the test for the bottom resistance, evaluating the concrete workability by using a calculation model of general coefficient for the concrete workability to solve the general coefficient for the concrete workability, the calculation model of the general coefficient for the concrete workability is as follows by integral calculation with an interval of v>100 mm/s:

$$W = \sum_{i=1}^{n} \int_{t_{i1}}^{t_{i2}} v(t) dt$$

wherein W is the general coefficient for the concrete workability, n is a number of the interval, $t_{i1}$ is a starting-point of the interval, $t_{i2}$ is an end-point of the interval, i=1,2, . . . , n.

2. The quantitative evaluation method for the concrete workability based on the bottom resistance analysis according to claim 1, wherein water and slurry float up from a segregated bleeding concrete, and sinking stones cement with a base tightly, resistance of aggregate is resulted at the bottom, and by determining a segregation degree of the concrete through a degree of the aggregate sank, cohesion and water retention of the concrete workability are quantitatively evaluated.

3. The quantitative evaluation method for the concrete workability based on the bottom resistance analysis according to claim 1, wherein the test for the bottom resistance of the fresh concrete is as follows:

mixing water, cement, grit, crushed stones and a water reducer according to a ratio to prepare the fresh concrete for use, wherein a mass ratio of the water, the cement, the grit to the crushed stones is 1:2.01:4.57:5.90, adding the water reducer having a gelling material mass of 0.22%-0.66%, filling the concrete container with the fresh concrete, upon sufficient vibration, wiping up the surface of the concrete container, fixing the steel sheet and a spring to a digital caliper with screws, pulling a vernier of the caliper to the bottom by using an insertion force provided by the spring, allowing the spring to be in a stress state, releasing the vernier so that a steel ruler on the vernier is inserted to the bottom of concrete with the coiled spring, and automatically recording the displacement of the steel sheet and the corresponding time by connecting the digital caliper to a computer.

4. The quantitative evaluation method for the concrete workability based on the bottom resistance analysis according to claim 1, wherein the test for the bottom resistance of the fresh concrete is as follows:

mixing water, cement, grit, crushed stones and a water reducer according to a ratio to prepare the fresh concrete for use, wherein a mass ratio of the water, the cement, the grit to the crushed stones is 1:2.01:4.57:5.90, adding the water reducer having a gelling material mass of 0.44%, filling the concrete container with the fresh concrete, upon vibration, wiping up the surface of the concrete container, fixing the steel sheet and a spring to a digital caliper with screws, pulling a vernier of the caliper to the bottom by using an insertion force provided by the spring, allowing the spring to be in a stress state, releasing the vernier so that a steel ruler on the vernier is inserted to the bottom of concrete with the coiled spring, and automatically recording the displacement of the steel sheet and the corresponding time by connecting the digital caliper to a computer.

* * * * *